(12) United States Patent
Myrick et al.

(10) Patent No.: US 8,352,205 B2
(45) Date of Patent: Jan. 8, 2013

(54) MULTIVARIATE OPTICAL ELEMENTS FOR NONLINEAR CALIBRATION

(75) Inventors: Michael L. Myrick, Irmo, SC (US);
Luisa Profeta, Richland, WA (US)

(73) Assignee: Halliburton Energy Services, Inc., Houston, TX (US)

( * ) Notice: Subject to any disclaimer, the term of this patent is extended or adjusted under 35 U.S.C. 154(b) by 556 days.

(21) Appl. No.: 12/528,101

(22) PCT Filed: Feb. 25, 2008

(86) PCT No.: PCT/US2008/054860
§ 371 (c)(1),
(2), (4) Date: Feb. 15, 2010

(87) PCT Pub. No.: WO2008/106391
PCT Pub. Date: Sep. 4, 2008

(65) Prior Publication Data
US 2010/0153048 A1    Jun. 17, 2010

Related U.S. Application Data

(60) Provisional application No. 60/903,919, filed on Feb. 28, 2007.

(51) Int. Cl.
*G01D 18/00* (2006.01)
*G01N 21/00* (2006.01)
*G06F 19/00* (2011.01)
*G06F 17/40* (2006.01)

(52) U.S. Cl. .......... 702/85; 73/1.02; 250/252.1; 702/24; 702/25; 702/88; 702/104; 702/187

(58) Field of Classification Search .................. 73/1.01, 73/1.02, 1.03, 1.06, 1.07, 1.88, 23.2, 23.21, 73/432.1, 865.8, 866; 250/252.1; 702/1, 702/22, 23, 24, 25, 30, 32, 85, 86, 88, 104, 702/127, 187, 189; 708/100, 105, 200
See application file for complete search history.

(56) References Cited

U.S. PATENT DOCUMENTS 3,211,913 A * 10/1965 Boimgren .................... 250/373
3,283,148 A * 11/1966 Schwarz et al. ........... 250/316.1
3,296,438 A *  1/1967 Main ........................... 250/364
(Continued)

FOREIGN PATENT DOCUMENTS
WO    WO 2006/064446 A1 *  6/2006

OTHER PUBLICATIONS

DeVerse, R. A. et al., "Realization of the Hadamard Multiplex Advantage Using a Programmable Optical Mask in a Dispersive Flat-Field Near-Infrared Spectrometer," Society for Applied Spectroscopy, 2000; vol. 54: pp. 1751-1758.

(Continued)

*Primary Examiner* — Edward Cosimano

(57) ABSTRACT

The present subject matter is direct to methodologies for calibrating data obtained from an optical analysis system. An initial calibration matrix of sampled analyte concentrations is modified using mean-centering techniques and selection of low and high analyte concentration spectra to produce a two-point calibration. A modified calibration matrix is produced by generating a non-linear calibration matrix by multiplying the initial calibration matrix by the two-point calibration. In an alternate embodiment, an initial multivariate optical element design is modified by iteratively adjusting the design based on standard error of calibration determination based on non-linerly fitted functions.

12 Claims, 3 Drawing Sheets

U.S. PATENT DOCUMENTS

| | | | | |
|---|---|---|---|---|
| 3,337,737 | A * | 8/1967 | Eberhardt | 250/207 |
| 3,470,381 | A * | 9/1969 | Boyd | 250/565 |
| 3,482,431 | A * | 12/1969 | Mochizuki | 73/23.2 |
| 5,612,782 | A * | 3/1997 | Keranen et al. | 356/243.8 |
| 5,641,962 | A * | 6/1997 | Perry et al. | 250/339.09 |
| 6,198,531 | B1 * | 3/2001 | Myrick et al. | 356/300 |
| 6,529,276 | B1 * | 3/2003 | Myrick | 356/419 |
| 6,549,861 | B1 * | 4/2003 | Mark et al. | 702/76 |
| 6,711,503 | B2 * | 3/2004 | Haaland | 702/22 |
| 7,123,844 | B2 * | 10/2006 | Myrick | 398/192 |
| 7,388,202 | B2 * | 6/2008 | Sterling et al. | 250/339.07 |
| 8,076,154 | B2 * | 12/2011 | Erickson et al. | 436/164 |
| 2002/0059047 | A1 * | 5/2002 | Haaland | 703/2 |
| 2002/0154315 | A1 * | 10/2002 | Myrick | 356/451 |
| 2006/0197015 | A1 * | 9/2006 | Sterling et al. | 250/252.1 |
| 2008/0112853 | A1 * | 5/2008 | Hall | 422/82.05 |
| 2009/0015819 | A1 * | 1/2009 | Van Beek et al. | 356/39 |
| 2009/0045342 | A1 * | 2/2009 | Sterling et al. | 250/339.09 |
| 2009/0150106 | A1 * | 6/2009 | Erickson et al. | 702/85 |
| 2009/0316150 | A1 * | 12/2009 | Myrick et al. | 356/326 |
| 2010/0221762 | A1 * | 9/2010 | Sterling et al. | 435/12 |

OTHER PUBLICATIONS

Myrick, M. L., et al., "A Single-Element All-Optical Approach to Chemometric Prediction," Vibrational Spectroscopy, 2002; vol. 28: pp. 73-81.

Myrick, M., "Multivariate Optical Elements Simplify Spectroscopy," Laser Focus World, 2002; vol. 38: pp. 91-94.

Haibach, F. G., et al., "Precision in Multivariate Optical Computing," Applied Optics, Apr. 2004; vol. 43, No. 10: pp. 2130-2140.

Prakash, AMC, et al., "Optical Regression: A Method for Improving Quantitative Precision of Multivariate Prediction With Single Channel Spectrometers," Chemometrics and Intelligent Laboratory Systems 46, 1999, pp. 265-274.

Soyemi, O. et al., "Design and Testing of a Multivariate Optical Element: The First Demonstration of Multivariate Optical Computing for Predictive Spectroscopy," Analytical Chemistry, Mar. 15, 2001, vol. 73, No. 6: pp. 1069-1079.

* cited by examiner

MULTIVARIATE OPTICAL ELEMENTS FOR NONLINEAR CALIBRATION

CROSS-REFERENCE TO RELATED APPLICATIONS

This application claims benefit of U.S. Provisional Patent Application Ser. No. 60/903,919, filed Feb. 28, 2007.

FIELD OF INVENTION

The present invention relates to the field of multivariate optical element design, manufacture and use. More specifically, the present invention relates to improvements related to the system design, fabrication and operation.

BACKGROUND OF THE INVENTION

Light conveys information through data. When light interacts with matter, for example, it carries away information about the physical and chemical properties of the matter. A property of the light, for example, its intensity, may be measured and interpreted to provide information about the matter with which it interacted. That is, the data carried by the light through its intensity may be measured to derive information about the matter. Similarly, in optical communications systems, light data is manipulated to convey information over an optical transmission medium, for example fiber optic cable. The data is measured when the light signal is received to derive information.

In general, a simple measurement of light intensity is difficult to convert to information because it likely contains interfering data. That is, several factors may contribute to the intensity of light, even in a relatively restricted wavelength range. It is often impossible to adequately measure the data relating to one of these factors since the contribution of the other factors is unknown.

It is possible, however, to derive information from light. An estimate may be obtained, for example, by separating light from several samples into wavelength bands and performing a multiple linear regression of the intensity of these bands against the results of conventional measurements of the desired information for each sample. For example, a polymer sample may be illuminated so that light from the polymer carries information such as the sample's ethylene content. Light from each of several samples may be directed to a series of bandpass filters that separate predetermined wavelength bands from the light. Light detectors following the bandpass filters measure the intensity of each light band. If the ethylene content of each polymer sample is measured using conventional means, a multiple linear regression of ten measured bandpass intensities against the measured ethylene content for each sample may produce an equation such as:

$$y = a_0 + a_1 w_1 + a_2 w_2 + \ldots + a_{10} w_{10} \quad \text{Equation 1}$$

where y is ethylene content, $a_n$ are constants determined by the regression analysis, and $w_n$ is light intensity for each wavelength band.

Equation 1 may be used to estimate ethylene content of subsequent samples of the same polymer type. Depending on the circumstances, however, the estimate may be unacceptably inaccurate since factors other than ethylene may affect the intensity of the wavelength bands. These other factors may not change from one sample to the next in a manner consistent with ethylene.

A more accurate estimate may be obtained by compressing the data carried by the light into principal components. To obtain the principal components, spectroscopic data is collected for a variety of samples of the same type of light, for example from illuminated samples of the same type of polymer. For example, the light samples may be spread into their wavelength spectra by a spectrograph so that the magnitude of each light sample at each wavelength may be measured. This data is then pooled and subjected to a linear-algebraic process known as singular value decomposition (SVD). SVD is at the heart of principal component analysis, which should be well understood in this art. Briefly, principal component analysis is a dimension reduction technique, which takes m spectra with n independent variables and constructs a new set of eigenvectors that are linear combinations of the original variables. The eigenvectors may be considered a new set of plotting axes. The primary axis, termed the first principal component, is the vector, which describes most of the data variability. Subsequent principal components describe successively less sample variability, until only noise is described by the higher order principal components.

Typically, the principal components are determined as normalized vectors. Thus, each component of a light sample may be expressed as $x_n z_n$, where $x_n$ is a scalar multiplier and $z_n$ is the normalized component vector for the $n^{th}$ component. That is, $z_n$ is a vector in a multi-dimensional space where each wavelength is a dimension. As should be well understood, normalization determines values for a component at each wavelength so that the component maintains it shape and so that the length of the principal component vector is equal to one. Thus, each normalized component vector has a shape and a magnitude so that the components may be used as the basic building blocks of all light samples having those principal components. Accordingly, each light sample may be described in the following format by the combination of the normalized principal components multiplied by the appropriate scalar multipliers:

$$x_1 z_1 + x_2 z_2 + \ldots + x_n z_n$$

The scalar multipliers $x_n$ may be considered the "magnitudes" of the principal components in a given light sample when the principal components are understood to have a standardized magnitude as provided by normalization.

Because the principal components are orthogonal, they may be used in a relatively straightforward mathematical procedure to decompose a light sample into the component magnitudes, which accurately describe the data in the original sample. Since the original light sample may also be considered a vector in the multi-dimensional wavelength space, the dot product of the original signal vector with a principal component vector is the magnitude of the original signal in the direction of the normalized component vector. That is, it is the magnitude of the normalized principal component present in the original signal. This is analogous to breaking a vector in a three dimensional Cartesian space into its X, Y and Z components. The dot product of the three-dimensional vector with each axis vector, assuming each axis vector has a magnitude of 1, gives the magnitude of the three dimensional vector in each of the three directions. The dot product of the original signal and some other vector that is not perpendicular to the other three dimensions provides redundant data, since this magnitude is already contributed by two or more of the orthogonal axes.

Because the principal components are orthogonal, or perpendicular, to each other, the dot, or direct, product of any principal component with any other principal component is zero. Physically, this means that the components do not interfere with each other. If data is altered to change the magnitude of one component in the original light signal, the other components remain unchanged. In the analogous Cartesian example, reduction of the X component of the three dimensional vector does not affect the magnitudes of the Y and Z components.

Principal component analysis provides the fewest orthogonal components that can accurately describe the data carried by the light samples. Thus, in a mathematical sense, the principal components are components of the original light that do not interfere with each other and that represent the most compact description of the entire data carried by the light. Physically, each principal component is a light signal that forms a part of the original light signal. Each has a shape over some wavelength range within the original wavelength range. Summing the principal components produces the original signal, provided each component has the proper magnitude.

The principal components comprise a compression of the data carried by the total light signal. In a physical sense, the shape and wavelength range of the principal components describe what data is in the total light signal while the magnitude of each component describes how much of that data is there. If several light samples contain the same types of data, but in differing amounts, then a single set of principal components may be used to exactly describe (except for noise) each light sample by applying appropriate magnitudes to the components.

The principal components may be used to accurately estimate information carried by the light. For example, suppose samples of a certain brand of gasoline, when illuminated, produce light having the same principal components. Spreading each light sample with a spectrograph may produce wavelength spectra having shapes that vary from one gasoline sample to another. The differences may be due to any of several factors, for example differences in octane rating or lead content.

The differences in the sample spectra may be described as differences in the magnitudes of the principal components. For example, the gasoline samples might have four principal components. The magnitudes $x_n$ of these components in one sample might be J, K, L, and M, whereas in the next sample the magnitudes may be 0.94 J, 1.07K, 1.13 L and 0.86M. As noted above, once the principal components are determined, these magnitudes exactly describe their respective light samples.

Refineries desiring to periodically measure octane rating in their product may derive the octane information from the component magnitudes. Octane rating may be dependent upon data in more than one of the components. Octane rating may also be determined through conventional chemical analysis. Thus, if the component magnitudes and octane rating for each of several gasoline samples are measured, a multiple linear regression analysis may be performed for the component magnitudes against octane rating to provide an equation such as:

$$y=a_0+a_1x_1+a_2x_2+a_3x_3+a_4x_4 \quad \text{Equation 2}$$

where y is octane rating, $a_n$ are constants determined by the regression analysis, and $x_1$, $x_2$, $x_3$ and $x_4$ are the first, second, third and fourth principal component magnitudes, respectively.

Using Equation 2, which may be referred to as a regression vector, refineries may accurately estimate octane rating of subsequent gasoline samples. Conventional systems perform regression vector calculations by computer, based on spectrograph measurements of the light sample by wavelength. The spectrograph system spreads the light sample into its spectrum and measures the intensity of the light at each wavelength over the spectrum wavelength range. If the regression vector in the Equation 2 form is used, the computer reads the intensity data and decomposes the light sample into the principal component magnitudes $x_n$ by determining the dot product of the total signal with each component. The component magnitudes are then applied to the regression equation to determine octane rating.

To simplify the procedure, however, the regression vector is typically converted to a form that is a function of wavelength so that only one dot product is performed. Each normalized principal component vector $z_n$ has a value over all or part of the total wavelength range. If each wavelength value of each component vector is multiplied by the regression constant $a_n$ corresponding to the component vector, and if the resulting weighted principal components are summed by wavelength, the regression vector takes the following form:

$$y=a_0+b_1+b_2u_2+\ldots+b_nu_n \quad \text{Equation 3}$$

where y is octane rating, $a_0$ is the first regression constant from Equation 2, $b_n$ is the sum of the multiple of each regression constant $a_n$ from Equation 2 and the value of its respective normalized regression vector at wavelength n, and $u_n$ is the intensity of the light sample at wavelength n. Thus, the new constants define a vector in wavelength space that directly describes octane rating. The regression vector in a form as in Equation 3 represents the dot product of a light sample with this vector.

Normalization of the principal components provides the components with an arbitrary value for use during the regression analysis. Accordingly, it is very unlikely that the dot product result produced by the regression vector will be equal to the actual octane rating. The number will, however, be proportional to the octane rating. The proportionality factor may be determined by measuring octane rating of one or more samples by conventional means and comparing the result to the number produced by the regression vector. Thereafter, the computer can simply scale the dot product of the regression vector and spectrum to produce a number approximately equal to the octane rating.

In a conventional spectroscopy analysis system, a laser directs light to a sample by a bandpass filter, a beam splitter, a lens and a fiber optic cable. Light is reflected back through the cable and the beam splitter to another lens to a spectrograph. The spectrograph separates light from the illuminated sample by wavelength so that a detection device such as a charge couple detector can measure the intensity of the light at each wavelength. The charge couple detector is controlled by controller and cooled by a cooler. The detection device measures the light intensity of light from the spectrograph at each wavelength and outputs this data digitally to a computer, which stores the light intensity over the wavelength range. The computer also stores a previously derived regression vector for the desired sample property, for example octane, and sums the multiple of the light intensity and the regression vector intensity at each wavelength over the sampled wavelength range, thereby obtaining the dot product of the light from the substance and the regression vector. Since this number is proportional to octane rating, the octane rating of the sample is identified.

Since the spectrograph separates the sample light into its wavelengths, a detector is needed that can detect and distinguish the relatively small amounts of light at each wavelength. Charge couple devices provide high sensitivity throughout the visible spectral region and into the near infrared with extremely low noise. These devices also provide high quantum efficiency, long lifetime, imaging capability and solid-state characteristics. Unfortunately, however, charge couple devices and their required operational instrumentation are very expensive. Furthermore, the devices are sensitive to environmental conditions. In a refinery, for example, they must be protected from explosion, vibration and temperature fluctuations and are often placed in protective housings approximately the size of a refrigerator. The power requirements, cooling requirements, cost, complexity and maintenance requirements of these systems have made them impractical in many applications.

Multivariate optical computing (MOC) is a powerful predictive spectroscopic technique that incorporates a multi-wavelength spectral weighting directly into analytical instrumentation. This is in contrast to traditional data collection routines where digitized spectral data is post processed with a computer to correlate spectral signal with analyte concentration. Previous work has focused on performing such spectral weightings by employing interference filters called Multivariate Optical Elements (MOEs). Other researchers have realized comparable results by controlling the staring or integration time for each wavelength during the data collection process. All-optical computing methods have been shown to produce similar multivariate calibration models, but the measurement precision via an optical computation is superior to a traditional digital regression.

Multivariate optical computing has been demonstrated to simplify the instrumentation and data analysis requirements of a traditional multivariate calibration, for example in "Multivariate optical elements simplify spectroscopy" by M. Myrick, Laser Focus World 38, 91-94 (2002). Specifically, the Multivariate Optical Element (MOE) utilizes a thin film interference filter to sense the magnitude of a spectral pattern. A no-moving parts spectrometer highly selective to a particular analyte may be constructed by designing simple calculations based on the filter transmission and reflection spectra as illustrated in "Design and testing of a multivariate optical element: The first demonstration of multivariate optical computing for predictive spectroscopy," by O. Soyemi, D. Eastwood, L. Zhang, H. Li, J. Karunamuni, P. Gemperline, R. A. Synowicki and M. L. Myrick, Anal. Chem. 73, 4393-4393 (2001) and "A single-element all-optical approach to chemometric prediction," by M. L. Myrick, O. Soyemi, J. Karunamuni, D. Eastwood, H. Li, L. Zhang, A. E. Greer and P. Gemperline, Vib. Spectrosc. 28, 73-81 (2002).

Other research groups have also performed optical computations through the use of weighted integration intervals and acousto-optical tunable filters, as in "Optical regression: a method for improving quantitative precision of multivariate prediction with single channel spectrometers," by A. M. C. Prakash, C. M. Stellman and K. S. Booksh, Chemom, Intell. Lab. Syst. 46, 265-274 (1999) and digital mirror arrays as in "Realization of the Hadamard multiplex advantage using a programmable optical mask in a dispersive flat-field near-infrared spectrometer," by R. A. DeVerse, R. M. Hammaker and W. G. Fateley, Appl. Spectrosc. 54, 1751-1758 (2000), and holographic gratings.

The measurement precision of digital regression has been compared to various optical computing techniques including MOEs, positive/negative interference filters and weighted-integration scanning optical computing in, for example, "Precision in multivariate optical computing" by F. G. Haibach and M. L. Myrick, Appl. Optics 43, 2130-2140 (2004).

In a high signal condition where the noise of the instrument is limited by photon counting, optical computing offers a higher measurement precision when compared to its digital regression counterpart. The enhancement in measurement precision for scanning instruments is related to the fraction of the total experiment time spent on the most important wavelengths. While the detector integrates or co-adds measurements at these important wavelengths, the signal increases linearly while the noise increases as a square root of the signal. Another contribution to this measurement precision enhancement is a combination of the Felgott's and Jacquinot's advantage which is possessed by MOE optical computing.

While various implementations of optical computing systems have been developed, and while various calibration methodologies have been developed, no design has emerged that generally encompasses all of the desired characteristics as hereafter presented in accordance with the subject technology.

SUMMARY OF INVENTION

The present invention is directed generally to an optical system for multivariate optical computing. Multivariate optical computing (MOC) is generally described in U.S. Pat. No. 6,198,531 B1 to Myrick et al. and in U.S. Pat. No. 6,529,276 B1 to Myrick as a predictive spectroscopy technique that incorporates a multi-wavelength spectral weighting directly into analytical instrumentation. Both of these patents are incorporated herein for all purposes by reference thereto.

Multivariate Optical Computing (MOC) is a method by which an analyte characteristic of interest is predicted via an optical regression using a specialized interference filter called a Multivariate Optical Element (MOE). Conventionally MOC, along with most other chemometric methods, operate under the assumption that any optical spectra being used in the construction of a calibration model are linearly related to the analyte concentration. Complications to these linear calibration approaches arise when sample qualities or multivariate spectra are not linearly related to concentration. All linear calibration methods are susceptible to these non-linear effects, thus we have developed methods for improving calibrations in the presence of such nonlinearities. These non-linear methods may be applied to Principal Component Regression (PCR), partial least squares (PLS), MOE design, and other approaches to calibration.

The present invention recognizes and addresses the disadvantages of prior art construction and methods. Accordingly, it is an object of the present invention to provide an improved system for deriving information from light. It is a further object of certain embodiments of the present invention to introduce nonlinear calibration procedures for use with multivariate optical computing design algorithms.

BRIEF DESCRIPTION OF THE DRAWINGS

A full and enabling disclosure of the present invention, including the best mode thereof, directed to one of ordinary skill in the art, is set forth in the specification, which makes reference to the appended figure in which.

Figure 1:
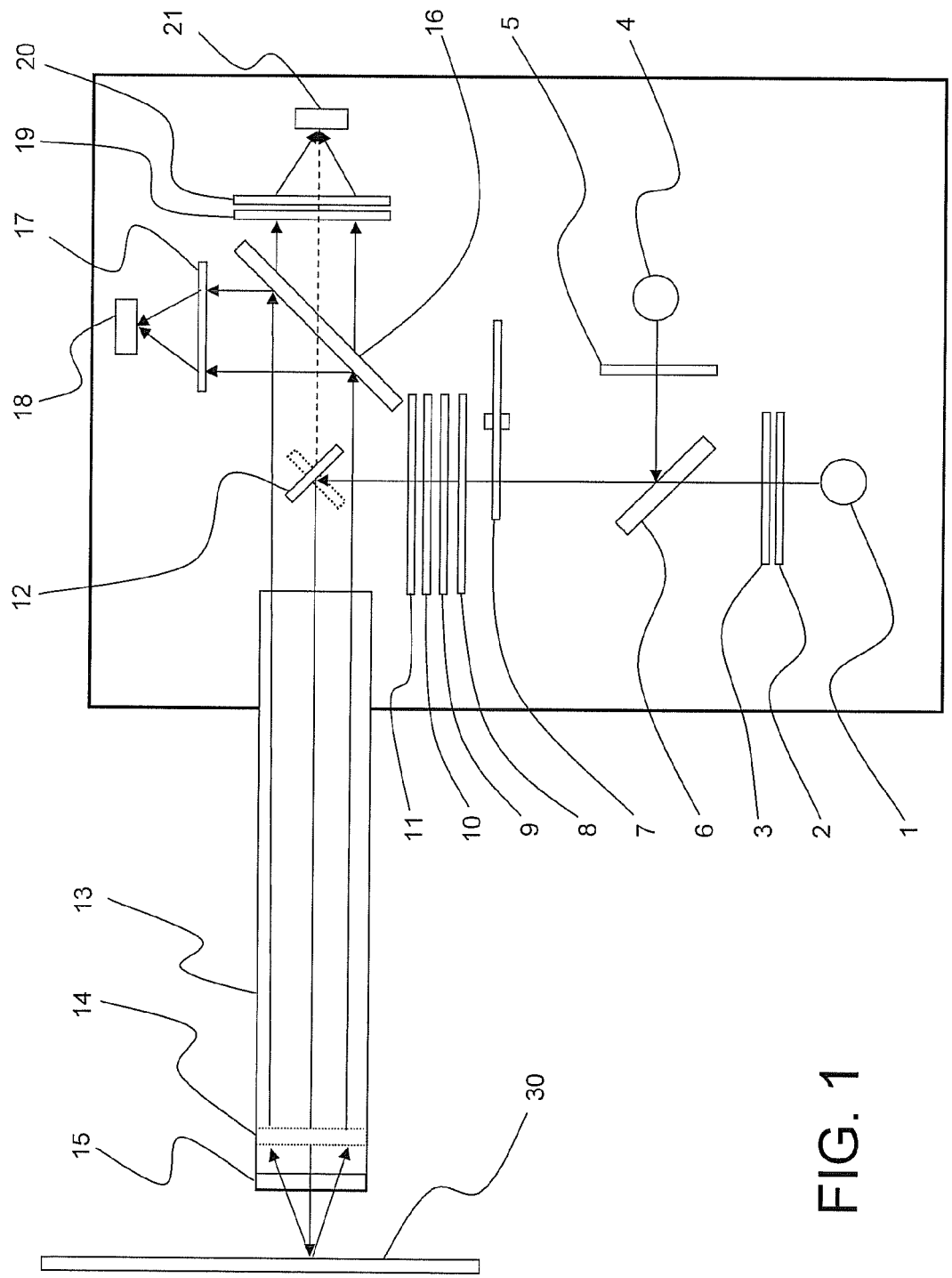
FIG. 1 illustrates an exemplary configuration of an optical analysis system constructed in accordance with the present subject matter.

Repeat use of reference characters throughout the present specification and appended drawing is intended to represent same or analogous features or elements of the invention.

DETAILED DESCRIPTION OF THE PREFERRED EMBODIMENTS

As discussed in the Summary of the Invention section, the present subject matter is particularly concerned with nonlinear calibration procedures for use with multivariate optical computing systems.

Selected combinations of aspects of the disclosed technology correspond to a plurality of different embodiments of the present invention. It should be noted that each of the exemplary embodiments presented and discussed herein should not insinuate limitations of the present subject matter. Features or steps illustrated or described as part of one embodiment may be used in combination with aspects of another embodiment to yield yet further embodiments. Additionally, certain features may be interchanged with similar devices or features not expressly mentioned which perform the same or similar function.

Reference will now be made in detail to the presently preferred embodiments of the subject nonlinear calibration methodologies. Referring now to the drawings, FIG. 1 illustrates an exemplary configuration of an optical analysis system constructed in accordance with the present subject matter.

The present subject matter discloses an optical analysis system as shown in FIG. 1 in which an illumination source corresponding in this exemplary configuration to illumination sources 1, 4 shine light through a set of lenses 2, 3, 5 and then through a multiple window chopper wheel 7 rotating at 40 Hz. In an exemplary configuration chopper wheel 7 may be configured with 10 windows. This produces a light beam modulated at 400 Hz. The light beam passes through one or several spectral elements or filters 8, 9, 10, and 11 which control the spectral region of the light which passes through them and onto a sample. The light is reflected by a turning mirror 12 down the center of a sampling tube 13 and focused by a lens 14 on the sample. Light is reflected back by the sample through the lens 14 and back down the sampling tube past the turning mirror 12. The light passes through a beam splitter 16 which reflects some of the light through a lens 17 onto a photodetector 18 and the other part of the light through a multivariate optical element (MOE) 19 and lens 20 and onto a photodetector 21.

The illumination sources 1, 4 used in this exemplary system are chosen to provide a spectral range as determined by the spectral range of interest for the measurement. The sources are also chosen based on reliability, intensity, temperature generation, and other factors. Redundant sources may be used to provide enhanced reliability. In some cases, when more sources are used, as exemplarily illustrated in FIG. 1, they could be oriented at 90 degrees from each other with a 50% beam splitter 6 located at the center point to provide a constant source of illumination through the chopper wheel 7.

One aspect to assembling a well performing system is to maximize the light levels through the system. As a result, there are many points in the design that are specified to enhance the transmission (reduce loss) of the light signal.

Lenses 2, 5 are used to collect the light from the illumination sources 1, 4 and then focus the light on the chopper wheel 7. Lenses 2 and 5 are designed and positioned to capture as much light as possible from the illumination sources. Lens 3 is used to focus as much light as possible through chopper wheel 7. The focal length, position and material of construction of the lenses are chosen to reduce as much as possible the loss of the light signal.

Chopper wheel 7 modulates the light signal (50-5000 Hz) to enable the photodetectors to perform properly. In one exemplary embodiment of the system, the system is operated with a 10-window chopper wheel rotating at 40 Hz, providing a chopped signal of 400 Hz. The chopper frequency is chosen based on several variables, including the rate of motion of the sample material past the sampling window, the performance characteristic of the photodetector and amplification system, the sampling rate of the data collection and analysis system and the physical properties of the chopper motor, control system, and wheel (including window materials).

The number of windows in the chopper wheel can be adjusted to provide a suitable degree of signal modulation. In the most basic design, the chopper consists of open windows and black spokes which block the light. In a further embodiment, different materials can be placed in the windows to provide different spectral characteristics for the various windows. These window materials are transmissive (at least somewhat) to the light signal and the transmission characteristic of these windows can be used as further spectral elements. These windows can also contain multivariate optical elements (MOEs).

After the light passes through chopper wheel 7, it passes through another lens and then through the spectral elements chosen based on the application, i.e., the chemical materials of interest. The spectral elements are chosen so that the spectral region of the illumination covers the desired range.

The light exits the spectral elements and reflects off of a mirror and down sampling tube 13. A lens 14 near the end of the tube near the sample focuses the light onto a sample material 30, with a focal point about 0-5 mm into the material. The end of sampling tube 13 can be sealed using a transmissive window 15. The lens 14 focuses the light past window 15 into the sample. Using such a window enables a vessel that is being tested/sampled into to remain intact. If the window is not uniformly transmissive across wavelengths, the transmission characteristics of the window should be taken into account for the design of the system and in particular the MOE.

Better separation of the illumination and reflection light paths can be further defined (separated) by physically separating the inner and outer regions with another tube. While a small reduction in total light return can be expected if such a tube is used (caused by the area of the outer tube physically occupied by the material of the inner tube), this loss may be more than offset by improvement in the amount of backscattered radiation returned to the detectors without ever encountering the sample.

The reflected light travels back down the outer annular region of sampling tube 13, past the turning mirror 12. The light reaches beam splitter 16 which divides the beam with a neutral or gray spectrum, sending some of the light through a lens 17 onto one detector 18 and some of the light through a Multivariate Optical Element (MOE) 19, then a lens 20 onto a second detector 21.

Because the system as described herein is completely enclosed, it can be used in a dangerous, explosive environment. In general, the system is contained in a box/housing of stainless steel, plastic or other material. The level of hazard of the environment determines the level of containment needed. The sampling is accomplished through a window that is transmissive in the spectral region of interest.

Multivariate optical computing operates on data in a transmission (T) mode. Conventional methods are usually applied to absorption (A) mode data because of the linearity of absorption spectra with chemical concentration that is implied by the Beer Lambert law. The relation between absorption and transmission modes is that $A=-\text{Log}(T)$. Since A is considered linear with concentration, T cannot be.

Linear calibration methods like PCR and the conventional design process for multivariate optical elements that has been previously described achieve linear calibrations in a nonlinear environment by finding regression vectors that are orthogonal to higher orders of the analyte spectrum. In normal MOC or PCR calculations there are two blocks of input data. The x block of data is a matrix that includes vectors corresponding to the spectral data of actual calibration samples. The y block of data corresponds to an array of numbers representing the true analyte values of interest. In an exemplary embodiment of the present subject matter these may correspond to calibration sample concentration.

Linearity is not generally necessary for a calibration to be successful, however, and different strategies have been developed by which data can be manipulated to compensate for non-linear properties in spectral data. The present technology introduces nonlinear calibration procedures that work with multivariate optical computing design algorithms, either by modifying the calibration data or by modifying the design algorithm. Three approaches are included herein as examples and embodiments of the present subject matter but are not intended to limit the scope of the invention.

In accordance with a first embodiment of the calibration methodology in accordance with the present technology, rather than calibrating to the analyte concentration, one can calibrate to the antilogarithm of the concentration. This has the effect of producing a y-block data array that is related to the transmission-mode data according to the Beer-Lambert law. This does not fix issues with nonlinear interferences with other components of the sample, but it has been shown to improve the quality of nonlinear calibrations.

In accordance with a second embodiment of the calibration methodology in accordance with the present technology, one can combine a calibration data set in a way to produce a modified calibration set that includes all the nonlinear spectral artifacts expected of a complex mixture in transmission mode, but that uses only a two-point analyte concentration vector. This results in a calibration that is generally curved if points between the two end-points are included. Such a modified calibration set is created as follows. Consider a conventional 5×5 matrix of sample concentrations with 5 levels of the analyte and 5 of an interferent species. If we take the samples at the same concentration levels of the analyte and perform an operation known as mean-centering (subtracting their average from each), the result is a set of spectra that reflect the vector of interferences for that particular level of analyte concentration. We perform this operation for each of the 5 analyte levels. The mean spectrum of the 5 low analyte concentration spectra and the mean spectrum of the 5 high analyte concentration spectra are calculated to serve as end-member spectra in a two-point calibration. To each of these averaged spectra is added the full set of mean centered spectra described previously. This produces 25 "low concentration" spectra and 25 "high concentration" spectra. These are then regressed via any desired method to obtain a regression vector describing the modified data set. This includes using the conventional linear MOE design algorithm to identify a predictive optical element for calibration.

The modified set regression vector is then applied to the original 5×5 calibration data by calculating the dot or direct product with each spectrum. These products are then regressed against the analyte concentration of the 25 calibration spectra. In general, this results in a curved relationship that can be conventionally curve-fit to linear, quadratic, cubic, or more exotic functional forms to generate a non-linear calibration. This has been shown to improve calibrations in the presence of non-linearity of the source data.

In accordance with a third embodiment of the calibration methodology in accordance with the present technology, a modification of the design function of the multivariate optical element design suite software is provided. Generally MOEs are designed by iterative solving to a linear function. The process works as follows: (1) An initial MOE design is selected. (2) The spectrum of the MOE is calculated. (3) The dot product of the MOE vector is calculated with each of the calibration spectra. (4) The best linear fit between the calibrated concentrations and the dot products is obtained. (5) This best linear fit is used to determine the standard error of the calibration (SEC). (6) A nonlinear optimization routine is used to optimize this SEC by modifying the design of the MOE.

In this third embodiment, this algorithm is changed in steps 4 and 5, in which the best quadratic or other nonlinear fitting function is chosen upon which to compute the SEC. If it is considered important to force the function to be single-valued (i.e. that a single calibrated concentration can only result from a single dot product over the range of calibration), then a mathematical test can be used to determine whether the function includes maxima or minima in the calibration range. If so, the optimization can be terminated, restarted, or replaced with a linear optimization until the nonlinear optimization does not fail the single-value test.

Figure 2:
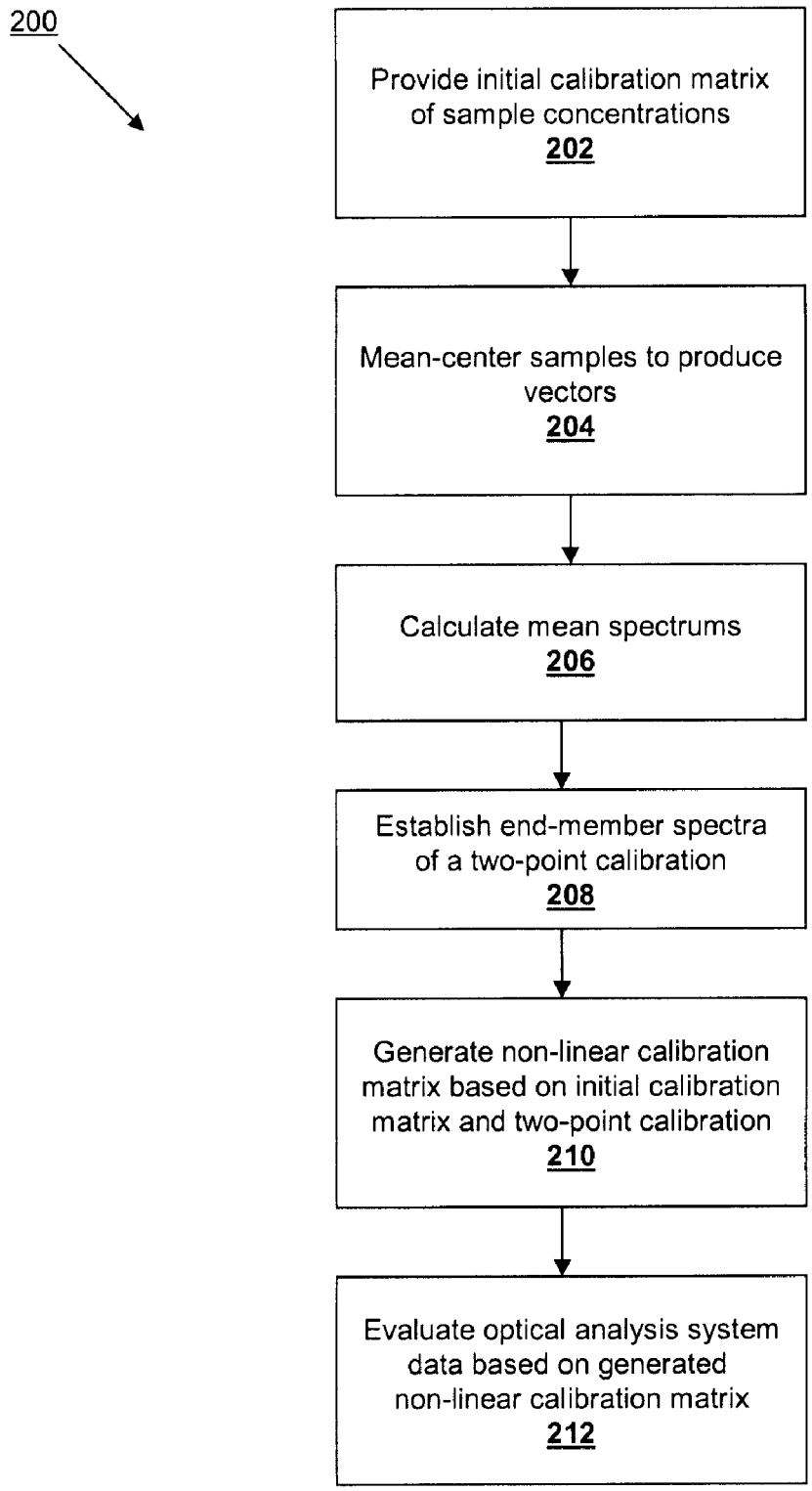
FIGS. 2 and 3 illustrate exemplary methodologies conducted in accordance with the present subject matter.

In view of the foregoing, and in reference to FIG. 2, exemplary methodologies of the present invention provide a method for calibrating data produced by an optical analysis system. This method 200 comprises, at step 202, providing an initial calibration matrix of sample concentrations including a first predetermined number of analyte concentration levels and a second predetermined number of levels of an interferent species. At step 204, the samples are mean-centered at each analyte concentration level to produce vectors representing interferences for the individual levels of analyte concentration. At step 206, the mean spectrum of the first predetermined number of levels of low and high analyte concentration spectra are calculated. At step 208, the calculated low analyte mean spectrum and the calculated high analyte mean spectrum are established as end-member spectra of a two-point calibration. At step 210, a non-linear calibration matrix is generated by multiplying the initial calibration matrix by the two-point calibration. Then, at step 212, the optical analysis system data is evaluated based on the generated non-linear calibration matrix.

Figure 3:
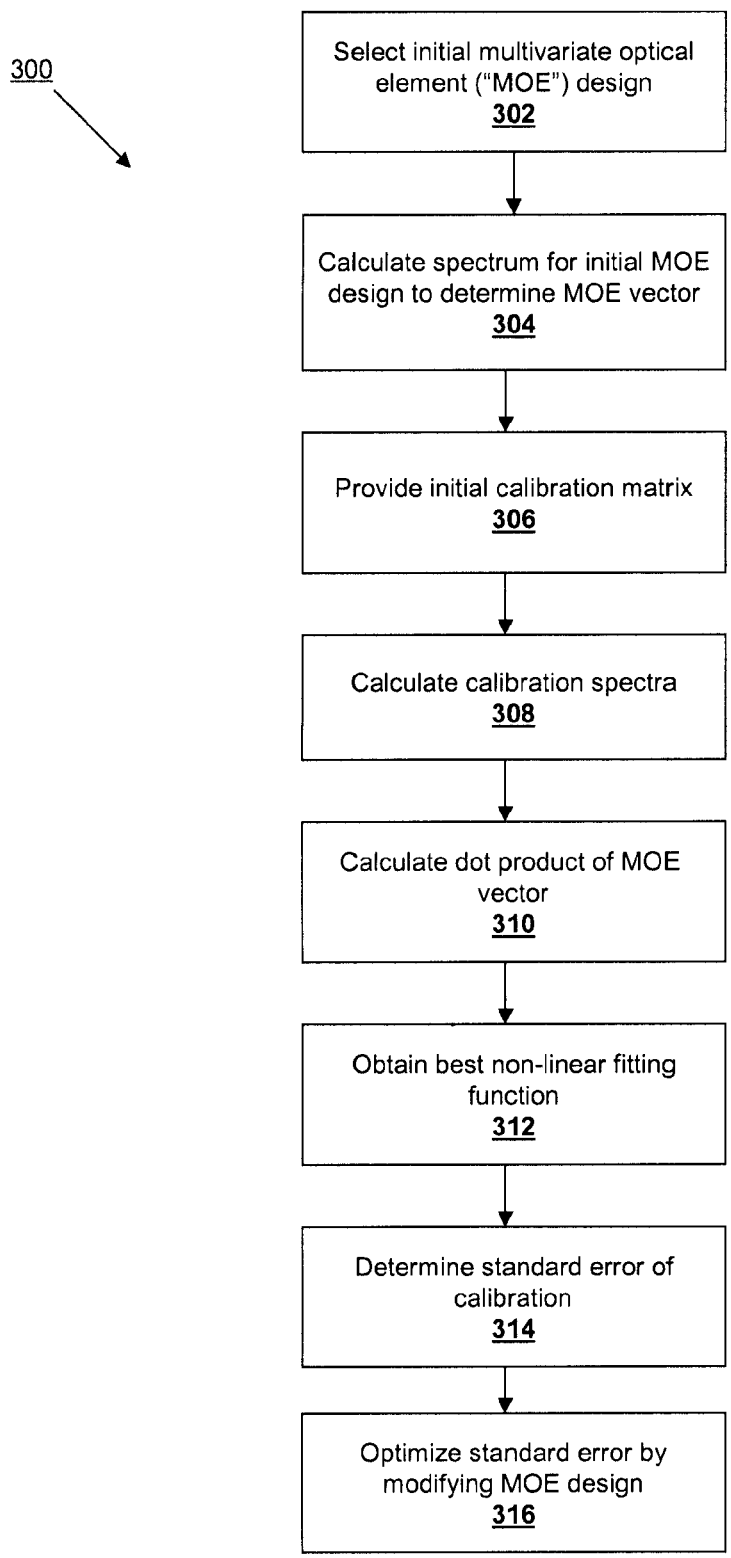

Also in view of the foregoing, and in reference to FIG. 3, another exemplary methodology of the present invention provides a method for calibrating data produced by a multivariate optical element analysis system. This method 300 comprises, at step 302, selecting an initial multivariate optical element ("MOE") design. At step 304, the spectrum for the initial MOE design is calculated to determine the MOE vector. At step 306, an initial calibration matrix of sample concentrations of a plurality of analyte concentrations and a plurality of levels of an interferent are provided. At step 308, calibration spectra are calculated based on the analyte concentration levels. At step 310, the dot product of the MOE vector is calculated with each calibration spectra. At step 312, the best non-linear fitting function is obtained between the calibration concentrations and the dot product. At step 314, the standard error of the calibration is determined. Thereafter, at step 316, the standard error of the calibration is optimized by modifying the MOE design.

While the present subject matter has been described in detail with respect to specific embodiments thereof, it will be appreciated that those skilled in the art, upon attaining an understanding of the foregoing may readily produce alterations to, variations of, and equivalents to such embodiments. Accordingly, the scope of the present disclosure is by way of example rather than by way of limitation, and the subject disclosure does not preclude inclusion of such modifications, variations and/or additions to the present subject matter as would be readily apparent to one of ordinary skill in the art.

What is claimed is:

1. A method for calibrating data produced by an optical analysis system, comprising:
   providing an initial calibration matrix of sample concentrations including a first predetermined number of analyte concentration levels and a second predetermined number of levels of an interferent species;
   mean-centering the samples at each analyte concentration level to produce vectors representing interferences for the individual levels of analyte concentration;
   calculating the mean spectrum of the first predetermined number of levels of low analyte concentration spectra;
   calculating the mean spectrum of the first predetermined number of levels of high analyte concentration spectra;
   establishing the calculated low analyte mean spectrum and the calculated high analyte mean spectrum as end-member spectra of a two-point calibration;
   generating a non-linear calibration matrix by multiplying the initial calibration matrix by the two-point calibration; and
   evaluating optical analysis system data based on the generated non-linear calibration matrix.

2. The method of claim 1, wherein providing an initial calibration matrix comprises:
   providing an initial calibration matrix of sample concentrations including five levels of analyte concentrations and five levels of an interferent species.

3. The method of claim 2, wherein generating a non-linear calibration matrix comprises:
   adding the mean-centered samples to each of the calculated low analyte concentration mean spectrum and the calculated high analyte concentration mean spectrum to produce a third predetermined number of low concentration spectra and a fourth predetermined number of high concentration spectra.

4. The method of claim 3, wherein the third and fourth predetermined number are each twenty-five.

5. The method of claim 3, further comprising:
   regressing the non-linear calibration matrix to obtain a modified set regression vector; and
   applying the modified set regression vector to the initial calibration matrix to obtain a modified set product.

6. The method of claim 5, wherein applying the modified set regression vector comprises calculating the dot product of the modified set regression vector with each spectrum.

7. The method of claim 5, wherein applying the modified set regression vector comprises calculating the direct product of the modified set regression vector with each spectrum.

8. The method of claim 5, further comprising:
   regressing the modified set product against the analyte concentration of the calibration spectra to obtain a curved relationship calibration function.

9. The method of claim 8, further comprising:
   fitting the curved relationship calibration function to one of a linear, quadratic, and cubic functional form to generate a non-linear calibration function.

10. A method for calibrating data produced by a multivariate optical element analysis system, comprising:
    selecting an initial multivariate optical element (MOE) design;
    calculating the spectrum for the initial MOE design to determine the MOE vector;
    providing an initial calibration matrix of sample concentrations of a plurality of analyte concentrations and a plurality of levels of an interferent;
    calculating calibration spectra based on analyte concentration levels;
    calculating the dot product of the MOE vector with each calibration spectra;
    obtaining the best non-linear fitting function between the calibration concentrations and the dot product;
    determining the standard error of the calibration; and
    optimizing the standard error of the calibration by modifying the design of the MOE.

11. The method of claim 10, further comprising:
    determining whether the best non-linear function includes maxima or minima.

12. The method of claim 10 wherein obtaining the best non-linear fitting function comprises:
    obtaining the best quadratic fitting function between the calibration concentrations and the dot product.

* * * * *